(12) United States Patent
Lovenvirth

(10) Patent No.: US 8,347,819 B2
(45) Date of Patent: Jan. 8, 2013

(54) PET LITTER BOX EMPLOYING ULTRAVIOLET IRRADIATION

(76) Inventor: Stewart Jeffrey Lovenvirth, Inman, SC (US)

( * ) Notice: Subject to any disclaimer, the term of this patent is extended or adjusted under 35 U.S.C. 154(b) by 215 days.

(21) Appl. No.: 12/845,906

(22) Filed: Jul. 29, 2010

(65) Prior Publication Data

US 2012/0025096 A1 Feb. 2, 2012

(51) Int. Cl.
*A61L 2/10* (2006.01)
*A01K 1/015* (2006.01)
*A01K 29/00* (2006.01)

(52) U.S. Cl. ............... 119/165; 250/504 R; 250/455.11; 250/365; 119/163; 119/161; 96/16

(58) Field of Classification Search ............. 250/455.11, 250/504 R, 365; 119/165, 163, 161; 96/16
See application file for complete search history.

(56) References Cited

U.S. PATENT DOCUMENTS

| | | | | |
|---|---|---|---|---|
| 4,998,504 A | * | 3/1991 | Ball | 119/168 |
| 6,776,822 B2 | * | 8/2004 | Johnson | 96/16 |
| 6,857,391 B1 | * | 2/2005 | Gantt | 119/163 |
| 7,490,578 B1 | * | 2/2009 | Mottard | 119/161 |

* cited by examiner

*Primary Examiner* — Nikita Wells
(74) *Attorney, Agent, or Firm* — H. John Rizvi; Glenn E. Gold; Gold & Rizvi, P.A.

(57) ABSTRACT

A litter box for pets is provided having a container defined by a bottom and side walls and a germicidal ultraviolet light lamp positioned parallel to the bottom of the container and around the interior peripheral edge of the container, whereby the light from the lamp has an unobstructed path to the absorbent granular material in the container. A motion detector may be provided to turn the lamp off and on when a pet approaches the litter box.

15 Claims, 3 Drawing Sheets

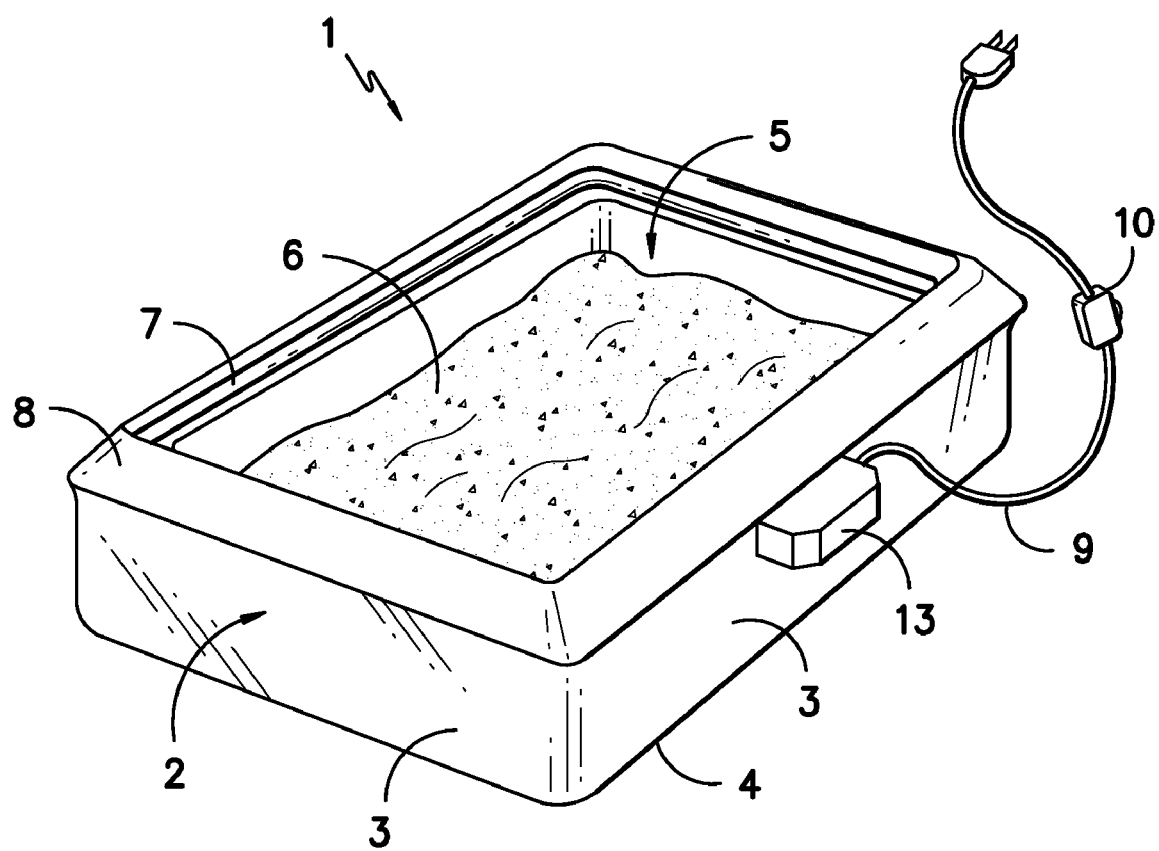
FIG. -1-

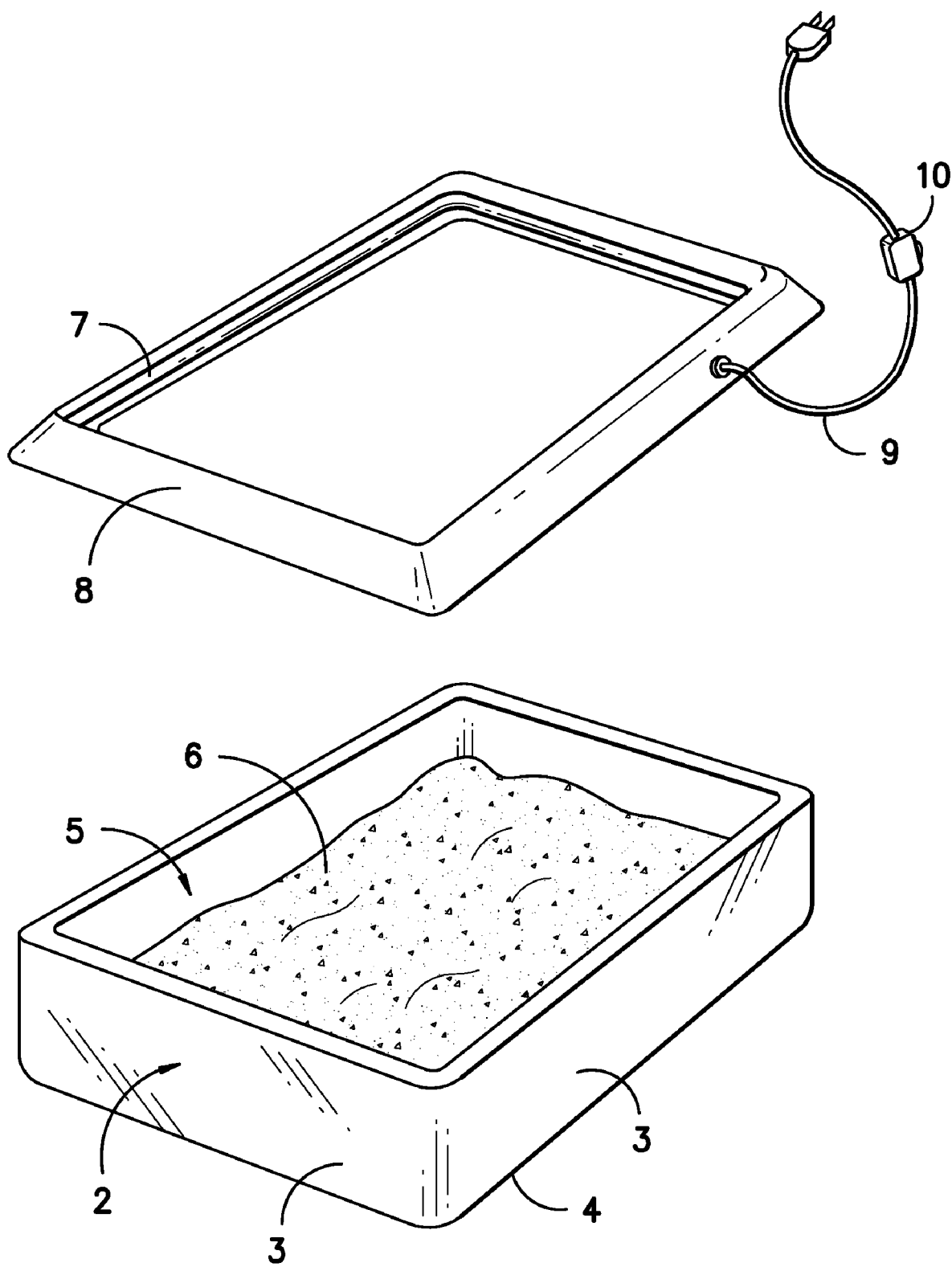
FIG. -2-

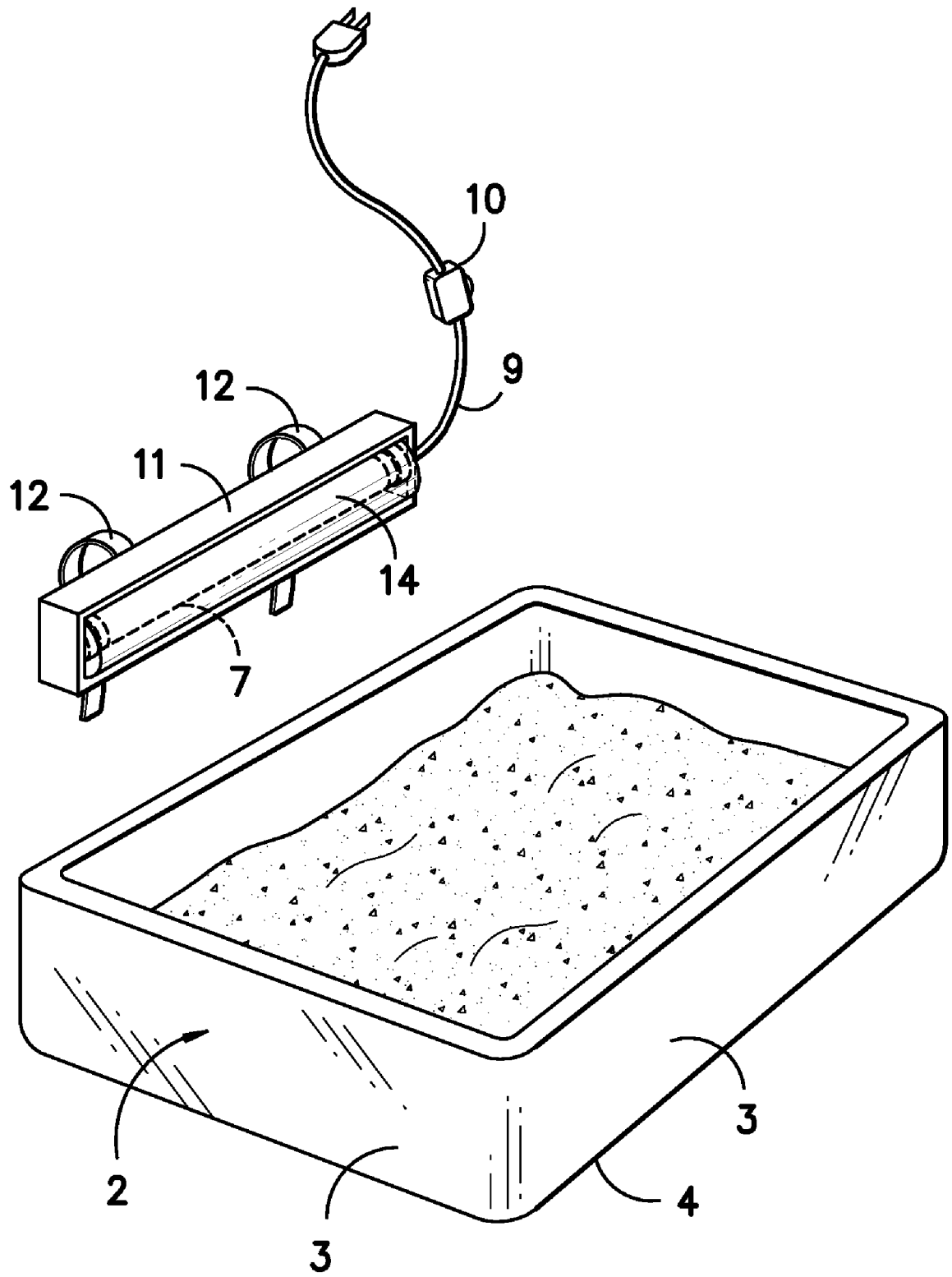
FIG. -3-

PET LITTER BOX EMPLOYING ULTRAVIOLET IRRADIATION

The present invention is directed towards a litter box for pets, which employs ultraviolet germicidal irradiation to reduce potentially harmful microorganisms.

BACKGROUND OF THE INVENTION

It is known that ultraviolet light of sufficiently short wavelength can be used to kill microorganisms. The ultraviolet light has a mutagenic effect on a microorganism's DNA, preventing reproduction and killing the microorganism. Ultraviolet light having a wavelength of 240-280 nm, also known as UV-C, appears to have the greatest germicidal properties.

Ball, U.S. Pat. No. 4,998,504 discloses a disposable pet litter box having a transparent container disposed within a sanitizing support container. Cat litter is placed in the transparent container. The support container has ultraviolet light producing lamps around its interior. The lamps, however, are exterior to the transparent container containing the litter. The UV light is transmitted though the transparent container and penetrates into the cat litter, to kill microorganisms.

Gantt, U.S. Pat. No. 6,857,391 discloses an animal toilet enclosure. The enclosure has floorboards arranged similar to louvers, which pivot to an open position, after the toilet has been used, to deposit the contents into a disposal hopper. Overhead ultraviolet and heat lamps may be provided in the enclosure to semi-sterilize and dry the floorboards.

The prior art devices suffer from various drawbacks, including lack of simplicity, high cost, and attenuation of the intensity of the ultraviolet light caused by transmission through plastic walls or the relative distance between the light source and material to be treated. Thus, there remains a need for an uncomplicated, inexpensive and effective method of treating litter boxes, to reduce potentially harmful microorganisms.

SUMMARY OF THE INVENTION

A litter box for pets, especially cats, is provided, having a germicidal, ultraviolet light producing lamp to kill microorganisms in the litter. The litter box includes a container having a bottom and side walls. The upper edges of the side walls define a periphery of the container. The shape of the container may be rectangular, circular or other geometry. Typically, the container is provided with a flat bottom, for stability. The side walls need not be the same height around the periphery of the container. For example, the side walls may be relatively high in most places, to prevent the litter from being thrown out, and be provided with a cut-out or notch, to allow a pet to easily enter and exit the interior of the container.

The container may be open from above. Alternatively, the container may be fitted with a domed cover, to reduce odor. The containers commonly used for pet litter boxes are opaque, for aesthetics and to minimize cost. By way of example, the sides of the litter box may range in height from 3 to 12 inches.

The litter box includes a source of germicidal, ultraviolet irradiation, such as a germicidal lamp that produces ultraviolet light (UV-C) having a wavelength of from 240-280 nm and with sufficient intensity to kill microorganisms exposed to the irradiation. By way of example, the lamp may be a low pressure or medium pressure lamp, as are known in the art.

The litter box is provided with means to support the UV-C lamp in a position parallel to the bottom of the container and along the side of the container, with a line-of-sight path to the upper surface of an absorbent granular material filled to a height of 4 inches, in the interior of the container. The ultraviolet lamp is positioned relative to the container so that the line-of-sight path between the lamp and the upper surface of the absorbent granular material in the container is "unobstructed," that is, the ultraviolet light does not pass through the container itself, before reaching the absorbent granular material.

The germicidal ultraviolet light producing lamp may extend along one or more sides of the container. For example, the lamp may extend along one, two, three or four walls of a rectangular container. In another embodiment of the invention, multiple sources of germicidal ultraviolet irradiation or lamps may be provided, which can be positioned along two sides of the container, for example on opposite sides, or along all sides of the container.

One means to support the germicidal ultraviolet lamp is a rim that engages the upper periphery of the container. For ease of cleaning, the rim may be detachable. Alternatively, the means for supporting the lamp may be clips that connect that lamp to the upper periphery of the container.

The litter box may be filled with an absorbent granular material, such a clay or sand, as is well known. Typically, the container is filled to a level of 2 to 4 inches with the absorbent material. The lamp may be positioned from 3 to 12 inches from the bottom of the container, in particular from 4 to 10 inches from the bottom of the container, to optimize the light intensity and area covered.

In one embodiment of the invention, the litter box is provided with a motion detector, which activates a switch to turn off the lamp, when a pet is in close proximity to the litter box. Disengaging the germicidal ultraviolet lamp when the pet approaches or enters the interior of the container is desirable both for pet safety and to avoid alarming the pet. By way of example the motion detector may be a passive infrared (PIR), ultrasonic or microwave based detector.

BRIEF DESCRIPTION OF THE DRAWINGS

FIG. 1 is a perspective view of the pet litter box.
FIG. 2 is an exploded view of the pet litter box.
FIG. 3 is a perspective view of an embodiment of the invention in which the ultraviolet lamp may clip on to the side of the pet litter box.

DETAILED DESCRIPTION OF THE INVENTION

Without intending to limit the scope of the invention, the preferred embodiments and features are hereinafter set forth. All United States patents cited in the specification are incorporated herein by reference.

Referring to FIG. 1, pet litter box 1 includes container 2 having side walls 3 and bottom 4. Container 2 is rectangular in shape, but can be provided in other geometries. Side walls 3 and bottom 4 define an interior 5, which contains an absorbent granular material 6.

An ultraviolet light producing lamp 7 is positioned along the upper peripheral edge of container 2, whereby lamp 7 is parallel to bottom 4 and extends along the interior of side walls 3. Means are provided to support lamp 7 in a position with an unobstructed, line-of-sight path to interior 5 of container 2 and the upper surface of absorbent granular material 6.

An electrical power cord 9, with on/off switch 10 is provided for lamp 7. Lamp 7 includes the components necessary to generate ultraviolet light having germicidal properties from an electric current, such as a ballast for triggering ionization and controlling the current. A side wall 3 of container 2 may be provided with a cavity, accessible from the exterior, for storing electrical cord 9 or portion thereof.

In one embodiment of the invention, the means to support lamp 7 is detachable rim 8, which houses lamp 7. Referring to FIG. 2, an illustration of rim 8 lifted from container 2 is shown. In an alternative embodiment of the invention shown in FIG. 3, the means to support lamp 7 is fixture 11, having brackets 12 for engaging the sides 3 of container 2. Additionally, as shown in FIG. 3, a cover 14 may be provided over lamp 7, to protect the lamp, as well as to protect a pet from electrical shock. Cover 14 should be selected from materials with maximum transmission of ultraviolet light in the germicidal wavelength (240-280 nm), such as fused silica quartz glass.

It can be understood that lamp 7 and the means to support lamp 7 in the desired position on container 2 may be provided separately, that is, as an after-market product to be added to a container. For example, rim 8, including lamp 7 and power cord 9, may be sold separately to be used with a suitably dimensioned container. Alternatively, fixture 11, lamp 7 and power cord 9, shown in FIG. 3, may be provided separately.

Referring to FIG. 1, lamp 7 is shown extending around the perimeter of container 2, in particular, along all four sides of the container. Other deployments of a single lamp or multiple lamps may be used, preferably around the interior of the side walls 3 or upper peripheral edges of the side walls 3 of container 2. For example, a single lamp 7 may be deployed along one, two or three sides of a rectangular container or partially around the perimeter of a container. Alternatively, multiple lamps may be deployed on two or more sides of container 2. For example, two lamps, such as the arrangement shown in FIG. 3, may be deployed on opposite sides of container 2.

Container 2 and rim 8, where applicable, may be made from a thermoplastic, thermosetting or elastomeric polymer, as is known to those skilled in the art. One method of manufacturing the parts is to inject mold a thermoplastic polymer resin. Alternatively, container 2 and/or rim 8 may be metal, such as sheet metal. By way of example, container 2 and/or 8 may be made of a reflective metal, such as aluminum or polished steel, to maximize the reflection of the ultraviolet light, thereby increasing the intensity and distribution of the light. Preferably, container 8 is opaque.

Referring to FIG. 1, ultraviolet light lamp 7 may optionally be controlled by motion detector 13. When a pet approaches the box, the motion detector will turn off the lamp, which has the advantages of protecting the pet from the potentially harmful ultraviolet light and avoiding alarming the pet. The motion detector can be set to turn back on the lamp, after a certain period of time, for example, ten minutes.

In an alternative embodiment of the invention, the motion detector may be set to turn on the lamp, a certain time after the approach of a pet is detected, and then to automatically turn off the lamp after a certain period of treatment time. For example, in one scenario, ten minutes after the motion detector senses the approach of the pet and presumably after the pet has used the litter box, the lamp is turned on for one hour, to sterilize the absorbent granular material.

The lamp of the subject invention may also be used in combination with various timing devices, to conserve electricity, as is known to those skilled in the art. For example, the lamp may be made to cycle on and off throughout the day.

The invention may be further understood by reference to the following claims.

What I claim is:

1. A litter box for pets, comprising:
   (a) a container having an interior defined by a bottom and side walls, wherein each of the side walls has an interior and exterior face;
   (b) a germicidal ultraviolet light producing lamp; and
   (c) a lamp supporting member, which supports the lamp in a position parallel to the bottom of the container and along an interior face of a side wall of the container, wherein the lamp is positioned to provide an unobstructed, line-of-sight path for the ultraviolet light to the interior of the container, wherein the lamp extends along the interior face of all of the side walls.

2. The litter box of claim 1, wherein the container is rectangular and the lamp extends along the interior face of at least two side walls.

3. The litter box of claim 1, wherein the lamp is positioned between 3 inches and 12 inches from the bottom of the container.

4. The litter box of claim 1, wherein the container is opaque.

5. The litter box of claim 4, wherein the litter box further comprises an absorbent, granular material.

6. The litter box of claim 1, further comprising a motion detector to control the lamp whereby the lamp is turned off when a pet is in close proximity to the container.

7. The litter box of claim 1, wherein the lamp supporting member is a detachable rim, which engages a periphery of the container.

8. The litter box of claim 6, wherein the container is rectangular and the lamp extends along the interior face of at least two side walls.

9. The litter box of claim 6, wherein the lamp is positioned between 3 inches and 10 inches from the bottom of the container.

10. A litter box for pets, comprising:
    (a) a container having a bottom, side walls and an upper peripheral edge formed by the side walls, wherein the bottom, walls and peripheral edge define an interior of the container and the container is open from above;
    (b) a germicidal ultraviolet light producing lamp positioned along the peripheral edge and parallel to the bottom of the container, wherein the lamp is positioned to provide a line-of-sight path for the ultraviolet light to the interior of the container at a height 4 inches from the bottom of the container, wherein the lamp extends along the interior face of all of the side walls.

11. The litter box of claim 10, wherein the lamp is positioned between 4 inches and 10 inches from the bottom of the container.

12. The litter box of claim 11, wherein the litter box further comprises an absorbent, granular material selected from the group comprising clay and sand.

13. The litter box of claim 10, further comprising a motion detector to control the lamp whereby the lamp is turned off when a pet is in close proximity to the container.

14. The litter box of claim 10, wherein the container is rectangular and the lamp extends along four sides of the container.

15. The litter box of claim 10, further comprising a detachable rim, which supports the lamp and engages a peripheral edge of the container.

* * * * *